United States Patent [19]

Clark et al.

[11] Patent Number: 5,786,598

[45] Date of Patent: Jul. 28, 1998

[54] STERILIZATION OF PACKAGES AND THEIR CONTENTS USING HIGH-INTENSITY, SHORT-DURATION PULSES OF INCOHERENT, POLYCHROMATIC LIGHT IN A BROAD SPECTRUM

[75] Inventors: Reginald Wayne Clark, Del Mar; James C. Lierman, San Diego; Donald Lander, La Jolla; Joseph E. Dunn, Vista, all of Calif.

[73] Assignee: PurePulse Technologies, Inc., San Diego, Calif.

[21] Appl. No.: 651,275

[22] Filed: May 22, 1996

[51] Int. Cl.$^6$ .................. B65B 55/08; A61L 2/10
[52] U.S. Cl. ..................... 250/455.11; 422/24
[58] Field of Search ................ 250/455.11; 422/24

[56] References Cited

U.S. PATENT DOCUMENTS

| | | | |
|---|---|---|---|
| 4,063,890 | 12/1977 | Baron | 422/24 |
| 4,282,863 | 8/1981 | Beigler et al. | 128/1 R |
| 4,464,336 | 8/1984 | Hiramoto et al. | 422/24 |
| 4,469,835 | 9/1984 | Laurin | 250/455.11 |
| 4,540,416 | 9/1985 | Hattori et al. | 604/410 |
| 4,629,658 | 12/1986 | Lucas | 428/520 |
| 4,657,540 | 4/1987 | Iwamoto | 604/408 |
| 4,866,282 | 9/1989 | Miripol et al. | 250/455.11 |
| 4,871,559 | 10/1989 | Dunn et al. | 422/24 |
| 5,122,126 | 6/1992 | Sakakiyama | 604/415 |
| 5,129,894 | 7/1992 | Sommermeyer et al. | 604/408 |
| 5,324,233 | 6/1994 | Owensby et al. | 493/190 |
| 5,494,155 | 2/1996 | Evans et al. | 206/204 |

FOREIGN PATENT DOCUMENTS

| | | |
|---|---|---|
| 2141723 | 1/1985 | United Kingdom . |
| 2117733 | 10/1993 | United Kingdom . |
| 82/01703 | 5/1982 | WIPO . |
| 88/03369 | 5/1988 | WIPO . |
| 9516565 | 6/1995 | WIPO . |

OTHER PUBLICATIONS

Dunn et al., "Pulsed–Light Treatment of Food and Packaging", Food Technology, vol. 49, No. 9, pp. 95–98, Sep. 1995.

*Primary Examiner*—Jack I. Berman
*Attorney, Agent, or Firm*—Fitch, Even, Tabin & Flannery

[57] ABSTRACT

An approach for sterilizing product containers and deactivating microorganisms in such containers employs the container, which, in one embodiment, includes a polyolefin, and which transmits light in a spectrum of from between 180 nm and 300 nm. The container may be coupled to a port through which a product within the container can be withdrawn, or, alternatively, may include a blister that together with a backing material forms a cavity in which a contact lens is contained. A flashlamp system generates high-intensity, short-duration pulses of polychromatic light in a broad spectrum. The pulses of light generated by the flashlamp illuminate the container and thereby deactivate microorganisms within the container. In some embodiments, the container contains a transmissive product that transmits more than about one percent of light at a wavelength of 260 nm. In further embodiments, the high-intensity, short-duration pulses of polychromatic light in a broad spectrum deactivate microorganisms both within the container and within the port. In additional embodiments, the flashlamp advantageously deactivates sufficient microorganisms to achieve a sterility assurance level of at least $10^{-6}$.

31 Claims, 2 Drawing Sheets

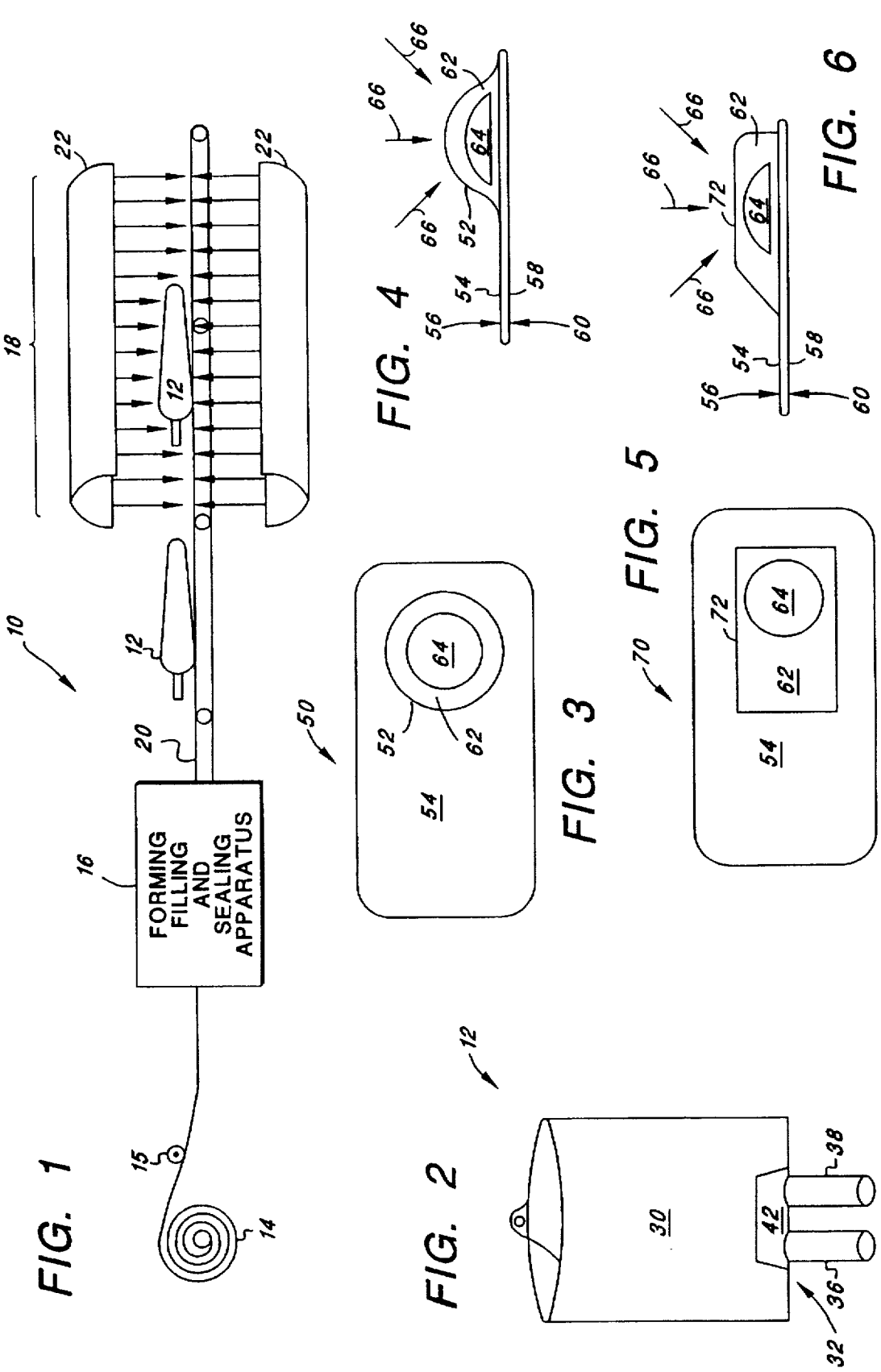

STERILIZATION OF PACKAGES AND THEIR CONTENTS USING HIGH-INTENSITY, SHORT-DURATION PULSES OF INCOHERENT, POLYCHROMATIC LIGHT IN A BROAD SPECTRUM

BACKGROUND OF THE INVENTION

The present invention relates to deactivation of microorganisms, and more particularly to the deactivation of microorganisms using high-intensity short-duration pulses of incoherent, polychromatic light in a broad spectrum. Even more particularly, the present invention relates to the deactivation of microorganisms within parenteral and/or enteral solutions and packages or within contact lens solutions and packages and/or ophthalmic solutions and packages using high-intensity, short-duration pulses of incoherent, polychromatic light in a broad spectrum directed at the packages filled and/or empty, so as to penetrate the packages and deactivate microorganisms, on an interior surface thereof and/or suspended within a product contained within the packages.

Polyvinyl Chloride (PVC) is a standard, widely used plastic packaging material used to manufacture flexible containers (bags and pouches) for the administration of small volume parenterals (SVPs), often referred to as mini-bags; large volume parenterals (LVPs); and various enteral nutritional and liquid preparations. These containers are often utilized for patient hydration and/or to supply pharmaceutical preparations, medicines, vitamins, nutritionals, and the like. Heretofore, PVC has proven to be advantageous because of its resistance to heat, which allows the containers to be terminally sterilized using high temperature treatment, i.e., sterilized after filling to deactivate microorganisms inside the containers, including microorganisms suspended in liquid content of the container, using high temperature treatment (e.g., autoclaving).

In many cases, an overwrap is also used to help the flexible containers to survive autoclaving, and also to increase the shelf life of parenteral fluids contained therein by providing improved moisture vapor barrier (MVB) properties, as compared to the MVB properties of PVC alone. In many cases, and particularly for SVP packages (or bags), multiple SVP packages are placed into one overwrap package. Disadvantageously, once the one overwrap package has been opened, the shelf life of the individual SVP packages contained therein is limited to approximately 30 days, because of the poor MVB properties of PVC. Thus, if a practioner opens an overwrap containing SVPs, but does not use all of the SVPs in a timely manner, the SVP packages must be discarded approximately 30 days after the overwrap is opened. The overwrap also represents a significant added packaging cost and contributes to environmental waste.

Using materials other than PVC, such as Olefins (e.g., Polyethylene or Polypropylene), nylon, or a composite material, either laminated or co-extruded structure (including both monolayer and multilayer structures), and the like, for SVP and/or LVP packages offers a number of significant advantages. One advantage is to reduce or eliminate the use of PVC because of environmental concerns. Another advantage of materials such as polyethylene is that they have much better MVB properties than PVC. For example, in some instances, it may be possible to achieve a longer shelf life (for example, 24 months verses the 15 to 18 months achievable with PVC and overwrap) without the inconvenience and added cost of the overwrap.

Another advantage to replacing PVC with a material such as polyethylene is that products such as pure deionized water (U.S.P. for injection) cannot be effectively packaged in PVC because by products from the PVC packaging material leach into the pure deionized water, contaminating it, whereas materials such as polyethylene do not contain by products that leach into the pure deionized water.

Enteral pre-filled packages also benefit in these ways.

Empty parenteral and enteral containers are also widely used, with liquid contents typically being manually added after delivery of the containers by a pharmacist or dietitian. These empty containers, heretofore typically produced in PVC, are often terminally sterilized using autoclaving. Unfortunately, these empty containers also suffer from the problems described above.

Thus, advantages exist to using olefin, nylon and composite material containers. However, heretofore known methods of terminal sterilization, such as autoclaving, are unsuitable for use with polyethylene containers or thin Polypropylene containers, because such containers are unable to withstand the temperatures (e.g., between 100 and 200° C.) used in autoclaving. (Polypropylene containers are able to withstand some amount of commercially useful autoclaving.) However, there exists a need for an approach to deactivating microorganisms in a container that does not require the use of heat that may damage the container or its contents.

Other processes, such as the process suggested by Beigler, et al. in the U.S. Pat. No. 4,282,863, entitled METHODS OF PREPARING AND USING INTRAVENOUS NUTRIENT COMPOSITIONS, issued Aug. 11, 1981, employ gamma radiation to achieve terminal sterilization. Unfortunately, the use of gamma radiation creates other problems. For example, gamma radiation is prone to altering the polymeric structure of the olefin container (i.e., gamma radiation degrades the product container integrity), which can result in weakened container integrity, leakage, increased gas permeability and other such problems. Furthermore, gamma radiation inherently causes the generation of highly reactive species, such as hydroxyl radicals, that may detrimentally alter the chemical structure of the product being treated. Thus, there exists a need for an improved sterilization process usable with polyolefins and the like that does not employ gamma radiation, or other such reactive processes, to achieve sterilization.

Other problems with heat treatment, i.e., autoclaving, and heretofore employed gamma radiation treatment techniques include the "batch" nature of such processes. Specifically, with heat or gamma radiation treatment, product containers are treated in groups or batches, which problematically requires careful inventorying and product handling in order to assure that each batch is segregated, and separately treated and tested.

With heretofore employed terminal sterilization techniques it is nearly impossible to monitor all of the parameters necessary to assure adequate deactivation of microorganisms in all of the product packages in a given batch. (For example, it is difficult to monitor the temperature within the autoclave at enough points than one can assure every part of every package in the batch received enough heat to achieve adequate deactivation of microorganisms.) Because such parametric control is not generally possible with autoclaving, such containers must be observed after a fourteen day period following autoclaving to determine whether any contaminants are present in selected (or all) containers from each batch. This unfortunately further complicates product and product container treatment and delays usage of the packages and products having been treated. An approach that can be performed in a continuous manner, e.g., as a part of a packaging process, thus eliminating the need for "batch" handling and "batch" testing, and that allows adequate parametric control over processing parameters needed to assure adequate sterility levels, thus eliminating the need for an observation period following treatment, would thus be highly advantageous.

It is generally accepted that terminally sterilized articles for medical or food applications, when processed, for example, in an autoclave, must attain a $10^{-6}$ survivor probability among microbial contaminants. In other words, there must be less than once chance in a million that viable microorganisms are present in a sterilized article. This level of sterilization is referred to as a sterility assurance level of $10^{-6}$.

Another approach to sterilization of parenteral and enteral containers involves presterilizing the containers using, for example, autoclaving, gamma radiation, chemical treatments or the like, and then filling such containers in an aseptic environment. A sterility assurance level of $10^{-6}$ is needed for most parenteral and enteral applications, and is difficult to verify using heretofore known aseptic filling approaches. (Current aseptic processes are validatable at sterility confidence levels of approximately $10^{-3}$. Sterility confidence level differs from sterility assurance level in that package integrity, or lack thereof, contributes to the sterility confidence level, whereas it does not contribute to sterility assurance level.) Thus, the U.S. Food and Drug administration, for example, has stated its preference for terminal sterilization processes, even though it recognizes that many products and product packages are damaged by such processes.

Therefore, what is needed is an approach to deactivating microorganisms in a container that achieves an easily verifiable sterility assurance level of at least, for example, $10^{-6}$, but reduces products and product containers damaged, such as can occur with current terminal sterilization techniques, such as autoclaving or gamma radiation treatment.

The present invention advantageously addresses the above and other needs.

SUMMARY OF THE INVENTION

The present invention advantageously addresses the needs above as well as other needs by providing an approach for deactivating microorganisms, and more particularly for the deactivating of microorganisms within parenteral and/or enteral solutions and packages or containers or contact lens solutions and packages and/or ophthalmic solutions and packages, and within product contents of such packages, using high-intensity, short-duration pulses of incoherent, polychromatic light in a broad spectrum directed at the packages, filled and/or empty, so as to penetrate the packages and deactivate microorganisms on an interior surface thereof and/or suspended within the product contained within the packages.

In one embodiment, the invention can be characterized as an apparatus for sterilizing microorganisms in a container. Such apparatus employs the container, which includes a polyolefin, and which transmits light in a spectrum containing wavelengths selected from between 120 nm and 2600 nm, e.g., wavelengths between 180 nm and 1500 nm or, e.g., between 180 nm and 300 nm. The container is coupled to a port through which a product within the container can be withdrawn. The port may be, for example, a plastic tube or cap having a puncture site at which it is designed to be punctured for administration of its contents, or may be a cap that is unscrewed or otherwise removed before administration. Such ports are well known in the art. A flashlamp system generates high-intensity, short-duration pulses of polychromatic light in a broad spectrum, and the pulses of light generated by the flashlamp illuminate the container and deactivate microorganisms within the container.

In a variation of this embodiment, an interface region at which the port is bonded to the container is also illuminated and microorganisms within the port and at the interface region are deactivated by the high-intensity, short-duration pulses of incoherent, polychromatic light in a broad spectrum.

In another embodiment, the invention may be characterized as an apparatus for deactivating microorganisms in a container that employs the container, which, in this embodiment, contains a transmissive product that transmits more than about one percent of light at a wavelength of 260 nm, and which container transmits light in a spectrum having wavelengths selected from between 120 nm and 2600 nm (see examples above). The embodiment also employs a port coupled to the container through which the product within the container can be withdrawn, and a flashlamp system that generates high-intensity, short-duration pulses of polychromatic light in a broad spectrum, and deactivates microorganisms within the container by illuminating the container with such pulses of light.

In a further embodiment, the invention can be characterized as an apparatus for deactivating microorganisms in a container. The apparatus of this embodiment employs the container, which in this embodiment transmits light in a spectrum including wavelengths selected from between 120 nm and 2600 nm (see examples above); and a port coupled to the container through which a product within the container can be withdrawn; and a flashlamp system that generates high-intensity, short-duration pulses of polychromatic light in a broad spectrum, and deactivates microorganisms within the container and port by illuminating the container and port with the pulses of light.

In an additional embodiment, the invention can be characterized as an apparatus for deactivating microorganisms in a container employing the container, which includes at least one port through which the product within the container can be withdrawn, and transmits light in a spectrum having wavelengths selected from between 120 nm and 2600 nm (see examples above); a flashlamp system that generates high-intensity, short-duration pulses of polychromatic light in a broad spectrum, and deactivates microorganisms within the container by illuminating the container with the pulses of light having been generated. The flashlamp of this embodiment advantageously deactivates sufficient microorganisms to achieve a sterility assurance level of at least $10^{-6}$.

In yet another embodiment, the invention can be characterized as an apparatus for sterilizing microorganisms in a container. The container of such embodiment includes a blister formed therein, and a backing material that together with the blister forms a cavity in which is contained a contact lens and a preservative fluid. The preservative fluid is at least one percent transmissive to light having a wavelength of 260 nm. A flashlamp system generates high-intensity, short-duration pulses of polychromatic light in a broad spectrum that deactivate microorganisms within the container by illuminating the container with the pulses of light having been generated.

BRIEF DESCRIPTION OF THE DRAWINGS

The above and other aspects, features and advantages of the present invention will be more apparent from the following more particular description thereof, presented in conjunction with the following drawings wherein:

FIG. 1 is a schematic diagram of an apparatus for fabricating, filling, sealing and sterilizing a parenteral or enteral package;

FIG. 2 is a side view diagram of an exemplary parenteral package suitable for use in a sterilizing chamber (or tunnel) of the apparatus of FIG. 1;

FIG. 3 is a top view of a contact lens package, having a "hemispherical" blister, and being suitable for use in the sterilizing chamber (or tunnel) of the apparatus of FIG. 1;

FIG. 4 is a side view of the contact lens package of FIG. 3, being suitable for use in the sterilizing chamber (or tunnel) of the apparatus of FIG. 1;

FIG. 5 is a top view of a contact lens package, having a "rectangular" blister, and being suitable for use in the sterilizing chamber (or tunnel) of the apparatus of FIG. 1;

FIG. 6 is a side view of the contact lens package of FIG. 5, being suitable for use in the sterilizing chamber (or tunnel) of the apparatus of FIG. 1;

Corresponding reference characters indicate corresponding components throughout the several views of the drawings.

DETAILED DESCRIPTION OF THE PREFERRED EMBODIMENTS

Figure 7:
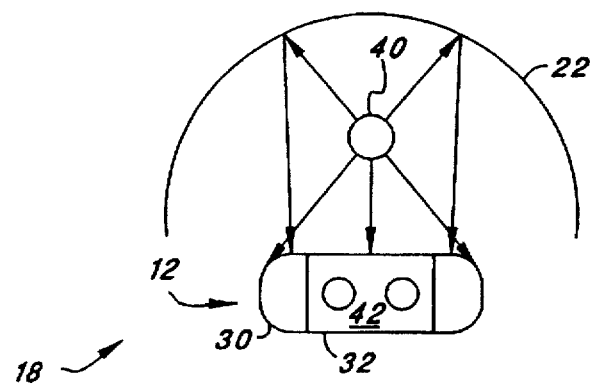
FIG. 7 is an end view of the parenteral package of FIG. 2 and one variation of a sterilizing chamber of the apparatus of FIG. 1.

The following description of the presently contemplated best mode of practicing the invention is not to be taken in a limiting sense, but is made merely for the purpose of describing the general principles of the invention. The scope of the invention should be determined with reference to the claims.

Referring first to FIG. 1, the diagram of an apparatus 10 for fabricating, filling, sealing, and sterilizing a parenteral or enteral package 12 is shown. A roll 14 (or other supply) of packing material is fed by, for example, rollers 15, into a fabricating, filling and sealing apparatus 16, such as are known in the art. Alternatively, the packaging material may assume a form of resin beads, as would be the case typically in a blow/ fill/seal apparatus. The fabricating, filling and sealing apparatus 16 may be a form/fill/seal apparatus; a blow/fill/seal apparatus; an injection blow molding apparatus; an extrusion and coextrusion blow molding apparatus; a film/sheet extrusion and coextrusion apparatus; a thermoforming apparatus; or an injection molding apparatus, such as are known in the art. Various sealing equipment and techniques may be employed including heat sealing, radio frequency (RF) fabrication, hot plate welding, induction welding, and/or spin welding, all of which are well known in the art.

Also shown, is a treatment zone, or sterilization tunnel, 18 (sterilizing chamber 18) through which fabricated, filled and sealed parenteral or enteral packages are passed, by, for example, a conveyer belt 20, in order to sterilize such packages. The conveyer belt 20 may employ one or more quartz shelves on which the parenteral or enteral packages rest while they are conveyed, or one or more hooks from which the parenteral or enteral packages hang while they are conveyed. In this way, the parenteral or enteral packages are not shielded from light as they pass through the sterilizing chamber 18.

The forming, filling and sealing apparatus 16 may, as mentioned above, be of a type well-known in the art, and preferably is capable of manufacturing containers (or packages) at high speeds, and with from one to multiple cavitations.

One example of a suitable blow/fill/seal apparatus adaptable for use with the present embodiment is marketed under Model No. 603 by Automatic Liquid Packaging, Inc. of Ill. Another such apparatus is marketed under Model No. 624 by Automatic Liquid Packaging of Ill.

A suitable form/fill/seal apparatus utilizes an extruded film to form a pouch or bag. One example of such a form/fill/seal apparatus adaptable for sue with the present embodiment is marketed as System Model Mark III by Inpaco of Pa.

Both the blow/fill/seal apparatuses and the form/fill/seal apparatus mentioned above permit the attachment of fitments (see FIGS. 2 and 2A) during formation of the package or container.

The sterilizing chamber 18, as shown, may consist of one or more reflectors 22, and one or more flashlamps (not shown), such as are available as Part No. 01812-525 from PurePulse Technologies, Inc. of San Diego, Calif. Such flashlamps and attendant pulse-generating hardware (not shown) are capable of generating high-intensity, short-duration pulses of incoherent polychromatic light in broad spectrum. Suitable flashlamps and attendant pulse generating hardware are described in U.S. Pat. Nos. 4,871,559 (METHODS FOR PRESERVATION OF FOODSTUFFS); 4,910,942 (METHODS FOR ASEPTIC PACKAGING OF MEDICAL DEVICES); and 5,034,235 (METHODS FOR PRESERVATION OF FOODSTUFFS), issued to Dunn, et al. (the '559, '942 and '235 patents, respectively), incorporated herein by reference.

The one or more reflectors 22 direct light from the flashlamps toward completed parenteral or enteral packages 12. Preferably, the reflectors 22 are made from, for example, aluminum, and optimally reflect light across the entire spectrum of light generated by the flashlamps. Advantageously, the reflectors may be designed, using commonly known design techniques, to create a uniform or non-uniform energy distribution of light across the parenteral or enteral package being illuminated. In this way, for example, greater amounts (i.e., concentrations) of light energy can be directed, for example, at thicker portions of the parenteral or enteral package, such as around an additive port and/or an administration port; and/or at portions of the product contained therein, such as near the middle of the parenteral or enteral package where a greater volume of produce needing treatment may be present.

In accordance with the present embodiment, the pulses of light pass through the parenteral or enteral packages 12, reaching the contents of such packages, and effecting sterilization or deactivation of microorganisms at the interior of the packages 12 and suspended within products contained in the packages 12.

In this way, an effective method is provided for sterilizing, not only parenteral or enteral packages, but product contents thereof, without requiring the high temperature processes involved in autoclaving. In addition, other product containers and products contained therein may be treated using the approach of this embodiment. For example, contact lens packages and the contact lenses contained therein can be treated using the above-approach. As a result, materials such as Olefins, nylon, and composite materials may advantageously be employed in product packages, instead of more conventional materials, such as polyvinyl chloride (PVC). Because Olefins, nylon, and composite materials have superior moisture vapor barrier characteristics to those of PVC, and do not contain components that are readily absorbed into the products contained, the above apparatus and attendant methods, provide a vastly superior forming, filling, sealing and sterilizing approach than has heretofore been available. Furthermore, the present embodiment achieves a sterility assurance level of at least $10^{-6}$, and does not require the use of gamma radiation or other highly degradative processes.

Referring to FIG. 2, a typical small volume parenteral 12 or large volume parenteral container 12 configuration is shown (generically referred to herein as a bag assembly 12). The bag assembly 12 employs a flexible pouch 30, made in the preferred embodiment from a polyolefin, such as polyethylene, to which a fitment 32 is joined. The fitment 32 generally includes two short tubes 36, 38 (or ports), through which a connection can be made for delivery of a liquid from the flexible pouch 30 (or parenteral pouch) to a feed tube (not shown), or to the flexible pouch, such as by a practitioner (often a pharmacist or nurse) when making an additive to the flexible pouch.

One port 36, the port used to make an additive, is typically referred to as an additive port 36, and another port 38, the port used for delivery of fluid, is typically referred to as an administration port 38. With a device referred to as an intravenous set (not shown), which is "spiked", i.e., punctured through, at the administration port 36, the flexible pouch's 30 contents can be delivered to a patient, either by gravity or with the use of a pump or controller (not shown).

Enteral containers (not shown), made preferably from polyolefins, such as polyethylene, utilize similar fitments, however, an enteral set (or spike set) and flexible tubing used with the enteral container is typically used to deliver liquid to a patient's stomach by a variety of methods, such as through a gastronomy tube for, for example, liquid feeding.

The flexible pouch 30 is preferably constructed of materials that transmit light in a spectrum of from, for example, between 180 nm and 1500 nm. Many materials, such as Polyethylene, Polypropylene, EVOH, nylon and a number of other plastic materials, either monolayer or multilayer, readily transmit this spectrum and can be used, in accordance with variations of the present embodiment.

Figure 2A:
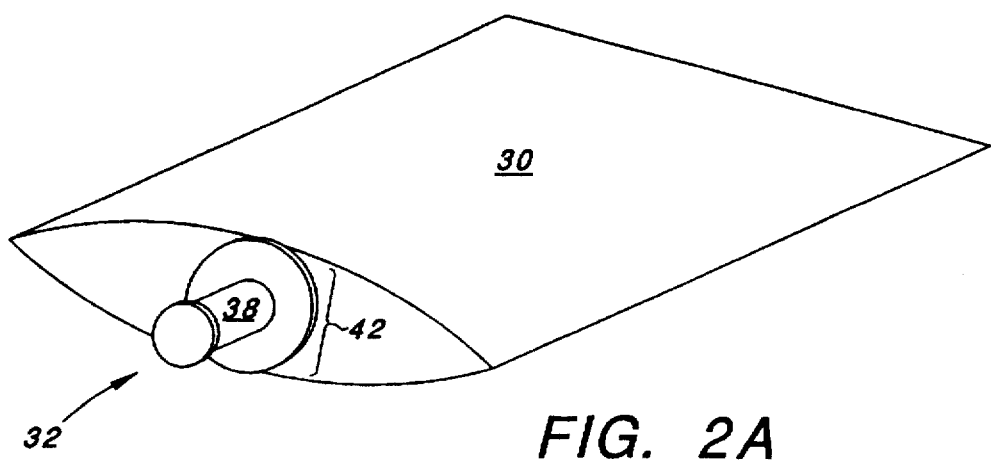
FIG. 2A is a perspective view of another exemplary parenteral package suitable for use in a sterilizing chamber (or tunnel) of the apparatus of FIG. 1.

The joining of the fitment 32 to the flexible pouch 30, and the filling of the flexible pouch 30, can preferably be conducted in an aseptic environment, such as a HEPA-filtered chamber, in a packaging machine, to minimize introduction of contaminants, such as microorganisms. (Such HEPA-filtered chambers are well known in the art.) The fitment 32 can be joined to the flexible pouch 30 by heat sealing, radio frequency (RF) welding or "plastic welding" techniques of the type commonly known in the art. An alternative example of a parenteral package suitable for use with the embodiment of FIG. 1 is shown in FIG. 2A.

Referring to FIG. 3, a top view is shown of a contact lens package 50, having a "hemispherical" blister 52, and being suitable for use in the sterilizing chamber (or tunnel). The contact lens package 50 has a polyolefin panel 54 (such as a polyethylene panel) into which is formed the blister 52. The blister 52 protrudes from a top side 56 (FIG. 4) of the polyolefin panel 56, and a foil backing 58 (FIG. 4) is adhered to the a bottom 60 of the polyoletin panel 54. Between the foil backing 58, and an interior of the blister 52 is formed a cavity 62 that is filled with a preservative fluid, such as saline solution, and a contact lens 67, such as a soft contact lens.

High-intensity, short-duration pulses of incoherent polychromatic light 66 (FIG. 4) are in practice directed at the top 56 of the polyolefin panel 54, and at the sides of the blister. The high-intensity, short-duration pulses of incoherent polychromatic light 66 (FIG. 4) have an intensity, duration, and wavelength or wavelengths as follows: intensity of from 0.01 J/cm$^2$ to 50 J/cm$^2$, e.g., 0.05 J/cm$^2$ to 5 J/cm$^2$, e.g., 2 J/cm$^2$; duration of from 0.001 ms to 100 ms, e.g., 0.3 ms; and wavelengths selected from between 120 nm and 2600 nm, e.g., wavelengths between 180 nm and 1500 nm or, e.g., between 180 nm and 300 nm. The high-intensity, short-duration pulses of incoherent polychromatic light 66 (FIG. 4) penetrate the blister 52, which is substantially transparent to light having wavelengths in the range selected, and impinge upon the preservative fluid and contact lens 64 contained therein. As a result, microorganisms at the interior of the blister 52, suspended in the preservative solution, and on or in the contact lens 64 are deactivated.

Advantageously, the contact lens 64 is sealed within the polyolefin package 50 prior to illumination of the package 50 with the high-intensity, short-duration pulses of incoherent polychromatic light, therefore preventing contamination of the interior of the blister, the preservative fluid, or the contact lens 64 following treatment (i.e., illumination). Also advantageously, the high-intensity, short-duration pulses of incoherent polychromatic light do not degrade the polyolefin panel 54, the foil 58, or the contact lens 64 contained thereinbetween.

Thus, a terminal sterilization approach is provided for use with a sealed contact lens package that, unlike heretofore known autoclaving and gamma radiation treatment approaches, does not result in degradation of the package being treated or the contact lens contained therein.

Referring to FIG. 4, a side view is shown of the contact lens package 50 of FIG. 3, being suitable for use in the sterilizing chamber (or tunnel) of the apparatus of FIG. 1. Shown are features of the contact lens package 50 of FIG. 3, with the top and the bottom of the package being more clearly identified, and with arrows representing the high-intensity, short-duration pulses of incoherent polychromatic light 66 as they are directed at the blister 52. Similar features bear similar reference numerals to those in FIG. 3.

Referring to FIG. 5, a top view is shown of a contact lens package 70, having a "rectangular" blister 72, and being suitable for use in the sterilizing chamber (or tunnel) of the apparatus of FIG. 1. The contact lens package 70 of FIG. 5 is substantially similar to the contact package 50 of FIG. 5, except that the blister 72 is generally rectangular in shape. The sterilization approach described above in reference to FIG. 3, however, can be employed with similar effectiveness to the contact lens package of FIG. 5. Features shown in FIG. 5 that are similar to features of FIG. 3 bear similar reference numerals.

Referring to FIG. 6, a side view is shown of the contact lens package 70 of FIG. 5, being suitable for use in the sterilizing chamber (or tunnel) of the apparatus of FIG. 1. Shown are features of the contact lens package of FIG. 5, with the top 56 and the bottom 60 of the package 70 being more clearly identified, and with arrows representing the high-intensity, short-duration pulses of incoherent polychromatic light 66 as they are directed at the blister. Similar features bear similar reference numerals to those in FIGS 3 and 5.

Referring next to FIG. 7, and end view is shown of the sterilizing chamber 18 of FIG. 1. In the variation shown, a single reflector 22 is positioned around a flashlamp 40 and above a parenteral container 12 as it is passed through the sterilizing chamber or, for example, a conveyor belt (not shown). The parenteral container 12 could easily be replaced by an enteral container or a contact lens container as applications demand.

In accordance with the present embodiment, high-intensity, short-duration pulses of polychromatic light in a broad spectrum are directed at the flexible pouch 30 and fitment 32 as they pass through the sterilizing chamber 18. Typically, the intensity of the pulses is from 0.01 J/cm$^2$ to 50 J/cm$^2$, e.g., 0.05 J/cm$^2$ to 5 J/cm$^2$, e.g., 2 J/cm$^2$. Advantageously, a high degree of deactivation of microorganisms within the flexible pouch 30, including deactivation of microorganisms suspended within fluid contained in the flexible pouch 30, deactivation of microorganisms at an interface 42 between the fitment 32 and the flexible pouch 30, and deactivation of microorganisms on or within the fitment 32, are effected by the pulses of light.

In some cases, the fitment 32 may not be sufficiently transmissive to permit complete sterilization of the fitment 32 with the high-intensity, short-duration pulses of polychromatic light in a broad spectrum. However, if a sufficiently transmissive material is selected for the fitment 32, and if an appropriate shape and thickness for the fitment is selected, such fitment 32 can be sufficiently sterilized with high-intensity, short-duration pulses of polychromatic light in a broad spectrum. Selection of a fitment design suitable for sterilization using high-intensity, short-duration pulses of polychromatic light in a broad spectrum is well within the abilities of the skilled artisan.

In accordance with the present embodiment and in the event the fitment cannot be completely sterilized using high-intensity, short-duration pulses of polychromatic light in a broad spectrum, an internal portion of the fitment 32 may be pre-sterilized with heat or gamma-radiation, before being joined to the flexible pouch. An interface region 42, such as shown best in FIG. 2A, at the periphery of the fitment 32, whereat the fitment 32 is joined to the flexible pouch 30, can be treated with the high-intensity, short-duration pulses of polychromatic light in a broad spectrum before and/or after the flexible pouch 30 is filled with fluid, thereby deactivating microorganisms at, in or near the interface region. Such pulses of light preferably have an intensity in the ranges mentioned above, i.e., 0.01 J/cm$^2$ to 50 J/cm$^2$, e.g., 0.05 J/cm$^2$ to 5 J/cm$^2$, or 2 J/cm$^2$ (measured at the interface of the fitment 32 with the flexible pouch 30).

The above-described pulsed light process uses high-intensity, short-duration pulses of polychromatic light in a broad spectrum, i.e., "white" light, to kill a wide range of microorganisms, including microbial and fungal spores. During each flash, the intensity of the light is about 20,000 times the intensity of sunlight at the earth's surface, i.e., the "high-intensity" of the light is from between 0.01 J/cm$^2$ to 50 J/cm$^2$, e.g., 0.05 J/cm$^2$ to 5 J/cm$^2$ or 2 J/cm$^2$, measured at the microorganisms to be deactivated. Each pulse, or flash, of light has a duration of only a fraction of a second (e.g., a "short-duration" of from between 0.001 ms to 100 ms, e.g., 0.3 ms).

The flashes are typically applied at a rate of about 1–20 flashes per second and, for most applications, a few, i.e., 1–3, flashes applied in a fraction of a second provide a very high level of microorganism deactivation, or kill. The duration of the light pulses is typically from between 200 and 300 µs.

The process of the present embodiment uses a technique referred to herein as pulsed energy processing. By storing electrical energy in a high energy density electrical storage capacitor, and releasing it in high-energy, short-duration pulses, high peak power levels are achieved. Such high-peak, power levels of electrical energy can be used to create the high-intensity, short-duration pulses of polychromatic light in a broad spectrum. (Pulsed energy processing is described in the '559, '942 and '235 patents, previously incorporated herein by reference.) The high intensity of these pulses of light results in a unique bactericidal effect not observed when the same energy is provided at low intensity in sustained or continuous wavelength (CW) applications. Although the peak power of each pulse is preferably very high, because of its short duration, the total energy in each pulse is relatively low, and the average power requirement ("wall plug power") is modest. Thus, the process is not only effective, but is economical with respect to energy consumption.

The pulses of light are generated by electrically ionizing a xenon gas lamp, causing it to emit broad band "white" light. A suitable flashlamp system for use with the present embodiment is readily available as Model No. PBS-1 or PBS-2 from Pure Pulse Technologies of San Diego, Calif., which model utilizes flashlamps, such as are, for example, available as Part No. 01812-525 from PurePulse Technologies, Inc. of San Diego, Calif. The emitted light pulses have wavelengths of from the far ultraviolet (200–300 nm), through the near ultraviolet (300–380 nm), and visible (380–780 nm), to the infrared (780–1100 nm). Approximately 25% of the energy distribution is ultraviolet, 45% of the energy distribution is visible, and 30% of the energy distribution of the light is infrared. Because only one to a few, i.e., 1–3, flashes of light are required to achieve microbial kill, and can be delivered in a very short period of time, this process can be administered very rapidly, and is usable in high throughput applications.

The light is non-ionizing, and does not penetrate opaque materials, but is transmitted through many packaging materials and therefore may be used to treat products while in the parenteral and enteral packages described above. The primary effects of treatment, and the main anti-microbial mechanisms, are believed to relate to the rich content of broad spectrum ultraviolet light, and the very high-intensity, short-duration nature of the pulses.

Figure 8:
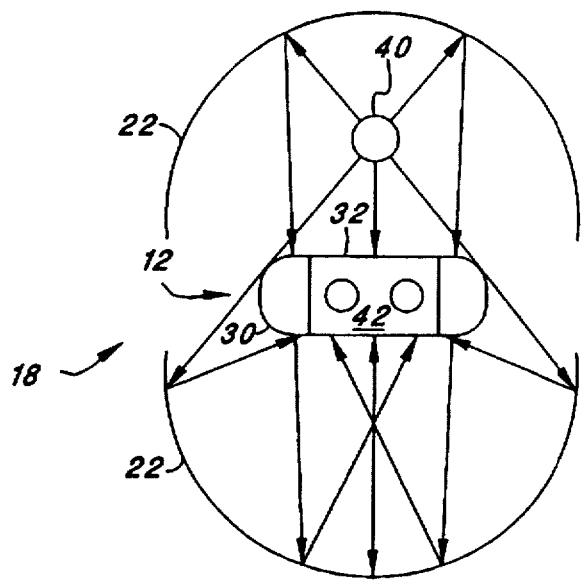
FIG. 8 is an end view of the parenteral package of FIG. 2 and another variation of the sterilizing chamber (or tunnel) of the apparatus of FIG. 1.

Referring next to FIG. 8, an end view is shown of the parenteral package of FIG. 2 in another variation of the sterilizing chamber 18 (or tunnel) of the apparatus FIG. 1. In the variation shown, a pair of reflectors 22 are positioned around a flashlamp 40 and the parenteral container 12, so as to form a tunnel, as the parenteral container is passed through the sterilizing chamber 18 on, for example, a conveyor belt (not shown). The variation shown functions in a manner similar to that in which variation of FIG. 7 functions except that light passing through, or passing by the parenteral container 12 after being emitted from the flashlamp 40, or reflected from an upper reflector 22, is reflected back toward the parenteral container 12 by a lower reflector 22. Advantageously, this variation maximizes the amount of light impinging upon the parenteral container 12, thereby maximizing the amount of light passing through the parenteral container 12 to deactivate microorganisms contained therein.

EXAMPLE 1

Flexible pouches of polyethylene are fabricated to contain 55 ml of either saline or dextrose. The flexible pouches are inoculated with 1 ml of a Clostridium sporogenes spore suspension (6.7 logs per ml.) or a *Bacillus pumilius* spore suspension (8.0 logs per ml.) and mixed. Inoculation control samples are collected from each bag with a sterile syringe in order to quantitate the numbers of viable inoculated spores recoverable from each bag for treatment.

The flexible pouches are then placed directly between two reflectors (such as shown in FIG. 8), forming a reflective cavity (or tunnel), and exposed to eight short-duration pulses of high-intensity, broad-spectrum, polychromatic light. After treatment, 1 ml of solution is removed from each bag and plated directly on tryptic soy agar (for the solution removed from the flexible pouches inoculated with *Clostridium sporogenes*) or standard methods agar (for the solution removed from the flexible pouches inoculated with *Bacillus pumilus*). The remainder of each flexible pouch is assayed for sterility by filtration. The experiment is repeated three times for each inoculum/solution combination (total of 12 tests: 3 saline/Clostridium; 3 dextrose/Clostridium; 3 saline/Bacillus; and 3 dextrose/Bacillus).

*Clostridium sporogene* spores are recovered from the saline filled flexible pouches before treatment at the concentration of 5 logs per ml (or 6.7 logs of spores per flexible pouch), and from the dextrose bags at 4.7 logs per ml (or 6.4 logs of spores per flexible pouch). *Bacillus pumilus* spores are recovered at the concentration of 6.5 logs per ml (or 8.2 logs of spores per flexible pouch) in the saline-filled flexible pouches, and at the concentration of 6.2 logs per ml (or 7.9 logs of spores per flexible pouch) in the dextrose solution samples before treatment. After treatment, no viable organisms are recovered from any of the samples, indicating that the treatment is capable of sterilizing the contents of parenteral pouches for each of the inoculum/solution combinations tested. Thus, EXAMPLE 1 achieves a sterility assurance level of $10^{-6}$.

EXAMPLE 2

Blow/fill/sealed polyethylene containers are filled to various volumes (0.5, 5, 15, and 300 ml) with water-for-injection. *Bacillus pumilus* spores (ATCC 27142), *Bacillus subtillus* strain *niger* var. *globigii* spores (ATCC 9372), and *Aspergillus niger* (ATCC 16404; containing conididiospores, hyphae and heads) are tested.

Six logs of each organism are inoculated by injection with a small gauge needle. Twelve replicate samples for each combination of organism, container volume, and treatment mode are inoculated. Two of the 12 samples serve as inoculation controls, and the small inoculation puncture is sealed directly with medical grade silicon sealant. Ten of the samples are treated with high-intensity, short-duration pulses of polychromatic light in a broad spectrum, before application of the medical grade silicon sealant in order to prevent shadowing of any sample volume by the sealant.

Two modes of treatment are tested. Containers are treated using a single lamp and reflector (such as shown in FIG. 7) illuminating each container from above with 20 flashes at 1.0 joules per centimeter per flash. In a second treatment mode, containers are treated in the reflective cavity (such as shown in FIG. 4) containing a single lamp with 20 flashes at 1.0 joules per cm squared per flash. These 0.5, 5 and 15 ml volumes are tested directly using 20, 20 and 60 ml pour plates respectively. The 300 ml volume samples are tested by filtration. In the single lamp and reflector (SLR) treatment mode, 36 of 40 A.niger samples are sterile, and all of the 40 *B.pumilus* and 40 *B.subtillus globigii* spore inoculated samples are sterile, i.e., free from viable microorganisms.

All samples treated using the cavity treatment mode are sterile, i.e., no viable organisms are recovered from any of the 120 individual samples tested. These results demonstrate that treatment with high-intensity, short-duration pulses of polychromatic light in a broad spectrum can sterilize water-for-injection in polyethylene containers inoculated at the six log level with three resistant strains of microorganisms. Thus, EXAMPLE 2 also achieves a sterility assurance level of $10^{-6}$.

While the invention herein disclosed has been described by means of specific embodiments and applications thereof, numerous modifications and variations could be made thereto by those skilled in the art without departing from the scope of the invention set forth in the claims.

What is claimed is:

1. An apparatus for sterilizing microorganisms in a container comprising:
   the container, wherein the container includes a polyolefin, and wherein the container transmits light in a spectrum of from between 180 nm and 300 nm;
   a port coupled to the container including means through which a product within the container can be withdrawn, and
   a flashlamp system including means for generating high-intensity, short-duration pulses of polychromatic light in a broad spectrum, and for deactivating microorganisms within the container by illuminating the container with the pulses of light having been generated.

2. The apparatus of claim 1 wherein said container consists of a polyolefin.

3. The apparatus of claim 1 wherein said container includes polyethylene.

4. The apparatus of claim 1 wherein said product is at least one percent transmissive to light having a wavelength of 260 nanometers.

5. The apparatus of claim 1 further comprising:
   an interface region whereat said port is bonded to said container;
   said flashlamp including means for deactivating microorganisms within the port by illuminating the port with the pulses of light having been generated, and for deactivating microorganisms at the interface region by illuminating the interface region with the pulses of light having been generated.

6. The apparatus of claim 1 wherein said means for deactivating includes means for achieving a sterility assurance level of at least $10^{-6}$.

7. The apparatus of claim 1 wherein said product includes at least one product from a group of products consisting of dextrose, saline solution, and sterile water.

8. An apparatus for deactivating microorganisms in a container comprising:
   the container, wherein the container contains a transmissive product that transmits more than about one percent of light at a wavelength of 260 nm, and wherein the container transmits light in a spectrum of from between 180 nm and 300 nm;
   a port coupled to the container including means through which the product within the container can be withdrawn; and
   a flashlamp system including means for generating high-intensity, short-duration pulses of polychromatic light in a broad spectrum, and for deactivating microorganisms within the container by illuminating the container with the pulses of light having been generated.

9. The apparatus of claim 8 wherein said container includes a polyolefin.

13

10. The apparatus of claim 8 wherein said container consists of a polyolefin.

11. The apparatus of claim 8 wherein said container includes polyethylene.

12. The apparatus of claim 8 further comprising:

an interface region whereat said port is bonded to said container;

said flashlamp including means for deactivating microorganisms within the port by illuminating the port with the pulses of light having been generated, and for deactivating microorganisms at the interface region by illuminating the interface region with the pulses of light having been generated.

13. The apparatus of claim 8 wherein said means for deactivating includes means for achieving a sterility assurance level of at least $10^{-6}$.

14. The apparatus of claim 8 wherein said product includes at least one product from a group of products consisting of dextrose, saline solution, and sterile water.

15. An apparatus for deactivating microorganisms in a container comprising:

the container, wherein the container transmits light in a spectrum of from between 180 nm and 300 nm;

a port coupled to the container including means through which a product within the container can be withdrawn; and a flashlamp system including means for generating high-intensity, short-duration pulses of polychromatic light in a broad spectrum, and for deactivating microorganisms within the container and port by illuminating the container and port with the pulses of light having been generated.

16. The apparatus of claim 15 wherein said container includes polyethylene.

17. The apparatus of claim 15 wherein said product is at least one percent transmissive to light having a wavelength of 260 nanometers.

18. The apparatus of claim 15 further comprising:

an interface region whereat said port is bonded to said container; and said flashlamp including means for deactivating microorganisms within the port by illuminating the port with the pulses of light having been generated, and for deactivating microorganisms at the interface region by illuminating the interface region with the pulses of light having been generated.

19. The apparatus of claim 15 wherein said means for deactivating includes means for achieving a sterility assurance level of at least $10^{-6}$.

20. The apparatus of claim 15 wherein said product includes at least one product from a group of products consisting of D5W, saline solution, and sterile water.

21. An apparatus for deactivating microorganisms in a container comprising:

the container, wherein the container includes at least one port through which the product within the container can

14 be withdrawn, and wherein the container transmits light in a spectrum of from between 120 nm and 2600 nm; and a flashlamp system including means for generating high-intensity, short-duration pulses of polychromatic light in a broad spectrum, and for deactivating microorganisms within the container by illuminating the container with the pulses of light having been generated, said means for deactivating including means for achieving a sterility assurance level of at least $10^{-6}$.

22. The apparatus of claim 21 wherein said container includes polyethylene.

23. The apparatus of claim 21 wherein said product is at least one percent transmissive to light having a wavelength of 260 nanometers.

24. The apparatus of claim 21 further comprising:

an interface region whereat said port is bonded to said container;

said flashlamp including means for deactivating microorganisms within the port by illuminating the port with the pulses of light having been generated, and for deactivating microorganisms at the interface region by illuminating the interface region with the pulses of light having been generated.

25. The apparatus of claim 21 wherein said product includes at least one product from a group of products consisting of D5W, saline solution, and sterile water.

26. An apparatus for sterilizing microorganisms in a container comprising:

the container, wherein the container includes a blister formed therein;

a backing material that together with the blister form a cavity in which is contained a contact lens and a preservative fluid;

a flashlamp system including means for generating high-intensity, short-duration pulses of polychromatic light in a broad spectrum, and for deactivating microorganisms within the container by illuminating the container with the pulses of light having been generated.

27. The apparatus of claim 26 wherein said container includes a polyolefin.

28. The apparatus of claim 26 wherein said container includes polyethylene.

29. The apparatus of claim 28 wherein said container transmits light in a spectrum of from between 180 nm and 300 nm.

30. The apparatus of claim 26 wherein said preservative fluid is at least one percent transmissive to light having a wavelength of 260 nanometers.

31. The apparatus of claim 26 wherein said means for deactivating includes means for achieving a sterility assurance level of at least $10^{-6}$.

\* \* \* \* \*